United States Patent

Kaptein

[11] Patent Number: 5,773,284
[45] Date of Patent: Jun. 30, 1998

[54] PHENYLSERINE AMIDES AND THE PREPARATION OF PHENYLSERINES/ PHENYLSERINE AMIDES

[75] Inventor: Bernardus Kaptein, Sittard, Netherlands

[73] Assignee: DSM N.V., Heerlen, Netherlands

[21] Appl. No.: 662,797

[22] Filed: Jun. 12, 1996

[30]     Foreign Application Priority Data

Dec. 17, 1993  [BE]  Belgium ................................ 09301405

[51] Int. Cl.$^6$ ............................... C12P 13/06; C12P 7/40; C12N 9/78; C07B 55/00
[52] U.S. Cl. ........................... 435/280; 435/116; 435/136; 435/170; 435/227; 435/228; 562/444; 562/401; 562/445; 562/567; 562/570
[58] Field of Search .................................... 435/116, 280, 435/136, 822, 227, 170, 228, 824, 852, 874; 562/444, 445, 567, 570, 401

[56]             References Cited

U.S. PATENT DOCUMENTS

| 3,971,700 | 7/1976 | Boesten .................................. 435/280 |
| 4,501,919 | 2/1985 | Koch et al. .............................. 562/437 |
| 5,215,897 | 6/1993 | Sakashita et al. ....................... 435/106 |
| 5,248,608 | 9/1993 | Van Dooren et al. .................. 435/280 |

FOREIGN PATENT DOCUMENTS

| 0 327 156 A1 | 8/1989 | European Pat. Off. . |
| 0 407 190 A2 | 1/1991 | European Pat. Off. . |
| 0 494 716 A2 | 7/1992 | European Pat. Off. . |
| 0 507 153 A2 | 10/1992 | European Pat. Off. . |
| 1 503 583 | 3/1978 | United Kingdom . |
| 2 182 036 | 5/1987 | United Kingdom . |

*Primary Examiner*—Ponnathapura Achutamurthy
*Assistant Examiner*—Padmashri Ponnaluri
*Attorney, Agent, or Firm*—Cushman Darby & Cushman, IP Group of Pillsbury Madison & Sutro, L.L.P.

[57]             ABSTRACT

Process for the preparation of a threo-phenylserine amide of the general formula 2 in which glycine amide is contacted with the corresponding substituted benzaldehyde of formula 3 in an excess relative to the amount of glycine amide, this taking place at a pH between 9 and 14 in the presence of a suitable solvent. The resulting phenylserine amide can subsequently be hydrolyzed to a phenylserine amide of the general formula 1, which is subsequently hydrolyzed to a phenylserine amide of the general formula 1, which is subsequently subjected to a stereoselective enzymatic hydrolysis yielding a (2S,3R) phenylserine. The non-hydrolyzed (2R,3S) phenylserine amide can be isolated as a Schiff base and be recirculated and simply racemized. The (2S,3R) phenylserine obtained can be used in the preparation of thiamphenicol or florfenicol. The threo-phenylserine amides of the general formula 1 or 2 are new intermediates in this commercially attractive process for the preparation of thiamphenicol and florfenicol.

14 Claims, No Drawings

PHENYLSERINE AMIDES AND THE PREPARATION OF PHENYLSERINES/PHENYLSERINE AMIDES

BACKGROUND OF THE INVENTION

1. Field of the Invention

The invention relates to threo-phenylserine amides and the preparation of such phenylserine amides and phenylserines. The phenylserine amides according to the invention are intermediates in a most advantageous process for the preparation of known chiral pharmaceuticals such as thiamphenicol and florfenicol, which are used in optically pure form.

2. Related Art

In the known processes for the preparation of the above-mentioned pharmaceuticals, as described for example in EP-A-407190, the route followed always goes via phenylserine compounds. However, it has been found that a highly advantageous process for the preparation of for example thiamphenicol and phlorophenicol can be obtained if a route is followed that initially goes via the phenylserine amide rather than via the acid (phenylserine).

SUMMARY AND OBJECTS OF THE INVENTION

The present invention therefore relates to the above-mentioned phenylserine amide intermediates, as racemate and in optically active form, their preparation and also their application in the preparation of pharmaceuticals.

The present process for the preparation of a threo-phenylserine amide represented by the general formula 2 involves contacting a glycine amide with the corresponding substituted benzaldehyde represented by formula 3 which is in an excess relative to the amount of glycine amide, the contacting taking place at a pH between 9 and 14, in the presence of a suitable solvent. The resultant phenylserine amide can subsequently be hydrolyzed to a phenylserine amide of the general formula 1. Subsequently, a stereoselective enzymatic hydrolysis can be conducted to yield a (2S, 3R) phenylserine. The non-hydrolyzed (2R, 3S) phenylserine amide can be isolated as a Schiff base and recirculated and simply racemized. The (2S, 3R) phenylserine which is obtained can be used in the subsequent preparation of thiamphenicol or florfenicol. The threo-phenylserine amides represented by the general formula 1 of general formula 2 are novel intermediates in the present commercially attractive process for the preparation of thiamphenicol or florfenicol.

DETAILED DESCRIPTION OF THE INVENTION

A first aspect of the invention relates to the threo-phenylserine amide compounds of formula (1)

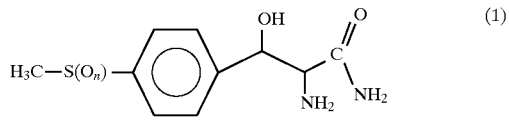

where n=0, 1 or 2 and the α-amino group may optionally be protected, and also to the Schiff base of these threo-phenylserine amides with a substituted benzaldehyde, according to formula (2)

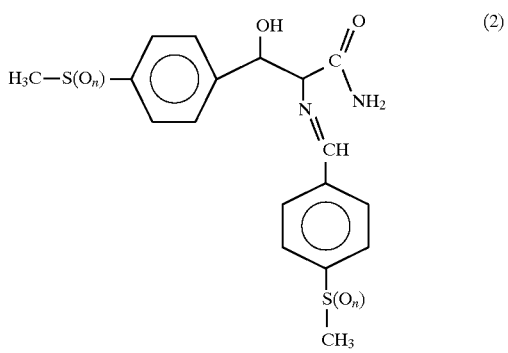

where n=0, 1 or 2.

Suitable amino protecting groups are the generally known amino protecting groups; in particular the amino group may be protonated, for example in the form of an HCl salt.

A second aspect of the invention relates to the preparation of the Schiff base of a threo-phenylserine amide compound of formula (2) and the preparation of the corresponding free phenylserine amide of formula (1), in which glycine amide is contacted with a substituted benzaldehyde of the general formula (3)

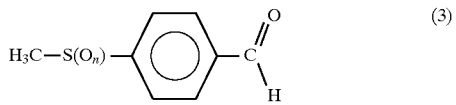

where n=0, 1 or 2 in an excess relative to the amount of glycine amide, this taking place at a pH between 9 and 14 in the presence of a suitable solvent.

The reason for this is that it has been found that, when glycine amide is started from, the threo form (a racemic mixture of the (2S,3R) and (2R,3S) enantiomers of the Schiff base of the phenylserine amide) surprisingly crystallizes out in high purity. The erythro compound (a racemic mixture of the (2S,3S) and (2R,3R) enantiomers remains in solution and is converted to the threo isomer, with less than 5% of the erythro compound remaining behind. The Schiff base can subsequently be hydrolyzed to the phenylserine amide of formula (1) in a known manner.

Another advantage of the route via the amide is that the desired (2S,3R) enantiomer can selectively be hydrolyzed to the corresponding (2S,3R) phenylserine from the mixture of (2S,3R) and (2R,3S) phenylserine amide, and this (2S,3R) phenylserine can subsequently be converted in a known manner to for example thiamphenol or phlorophenicol. It has been found that a high enantiomer excess (e.e.) can be achieved in an enzymatic hydrolysis with the aid of a suitable enzyme. The (undesired) (2R,3S) phenylserine amide can subsequently be isolated and optionally recovered.

It has moreover been found that the Schiff base of the (undesired) (2R,3S) phenyl glycine amide racemizes under the (basic) reaction conditions that are created in the preparation of the Schiff base of the phenylserine amides from glycine amide and the corresponding substituted benzaldehyde, so that (2S,3R) phenylserine with a high e.e. can be obtained in a particularly attractive process via recirculation of the undesired enantiomer. The invention therefore also relates to such a process for the preparation of a (2S,3R) phenylserine.

The preparation of the Schiff base of phenylserine amide from glycine amide and substituted benzaldehyde usually takes place at a temperature between 0° and 50° C., for example at room temperature. The pH at which this reaction is carried out preferably lies between 11 and 13. The molar ratio of glycine amide to substituted benzaldehyde usually lies between 1:3 and 2:3, preferably between 1:1.8 and 1:2.2. The highest yield is obtained at a molar ratio of almost 1:2.

Examples of suitable solvents are polar, water-miscible solvents, for example lower alcohols with 1–4 carbon atoms, optionally in combination with water. Preferably, as solvent use is made of a mixture of methanol in water, with a volume ratio of methanol to water of between 1:1 and 1:2, for example.

The resulting Schiff base of phenylserine amide can subsequently be hydrolyzed with an acid, usually a mineral acid, for example a hydrogen halogenide, to the salt of the free amide, which usually takes place at a pH between 0 and 2. The temperature at which the hydrolysis takes place usually lies between 20° and 50° C.; the hydrolysis is preferably effected at room temperature. Via neutralization the free amide can be obtained from the salt, if desired.

Examples of suitable enzymes that can be used in the enantio-selective enzymatic hydrolysis of the threo-phenylserine amides according to the invention are enzymes originating from the genera *Ochrobactrum, Achromobacter, Klebsiella* and *Pseudomonas,* for example *Ochrobactrum anthropi, Klebsiela oxytoca* and *Pseudomonas putida.* Use is preferably made of *Ochrobactrum anthropi* NCIB 40321 or *Klebsiella* sp. NCIB 40322, as described in EP-A-494716. The pH at which the enzymatic hydrolysis is carried out will in practice usually lie between 4 and 9, preferably between 5 and 8. It has been found that at this relatively low pH the substrate is dissolved and a high activity of the enzyme is still achieved. The enzymatic hydrolysis is usually carried out at ambient temperature or at a slightly elevated temperature, for example at a temperature between 0° and 85° C. Preferably, a temperature between 20° and 60° C. is maintained. It goes without saying that the reaction conditions are chosen so that no or only a minimum number of interfering side reactions occur.

After the enzymatic hydrolysis a mixture is obtained which mainly contains (2R,3S) phenylserine amide and (2S,3R) phenylserine. The undesired (2R,3S) phenylserine amide can subsequently be separated in a known manner. A very suitable method in the framework of the invention is obtained by converting the phenylserine amide, for example using a substituted benzaldehyde of formula (3), to the Schiff base and separating out the Schiff base formed, for example via filtration or extraction with a suitable extraction agent. Examples of suitable extraction agents are toluene, methyl-t-butylether, dichloro methane and chloroform. The Schiff base of (2R,3S) phenylserine amide can subsequently be returned to the reaction mixture, in which the glycine amide is contacted with the substituted benzaldehyde, upon which racemization takes place.

The (2S,3R) phenylserine obtained after the enzymatic hydrolysis can subsequently be converted in a known manner to the desired pharmaceutical, for example as described in EP-A-507153. Thus, for example, thiamphenicol can be prepared in a known manner from (2S,3R)-3-[4-(methylsulphonyl)phenyl]serine via esterification, followed by reduction of the resulting ester to the corresponding diol (1R,2R)-(3-[4-(methylsulphonyl)-phenyl]serinol), after which thiamphenicol is obtained via dichloro-acetylation. If (2S,3R)-3-[4-methylsulphanyl)phenyl)serine is started from, thiamphenicol can be obtained via oxidation of the product obtained after esterification, reduction and dichloro-acetylation, use being made of a suitable oxidation agent, for example peracetic acid and hydrogen peroxide, optionally in combination with a catalyst. Florfenicol can be obtained, for example, via fluorination of thiamphenicol, or of the diol obtained after esterification and reduction (in which case the amino group needs to be protected), followed by dichloro-acetylation and, optionally, oxidation.

Preferably, however, the conversion of a (2S,3R) phenylserine to the corresponding diol is carried out in one step using a suitable hydride as reduction agent, for example borane. The borane may optionally be formed in situ from other boron compounds, for example sodium borohydride ($NaBH_4$), in combination with an acid, for example a Lewis acid or a mineral acid. The resulting diol can, if desired, be isolated and purified, for example via formation of the Schiff base with the aid of benzaldehyde, extraction of the Schiff base, and hydrolysis to diol with the aid of, for example, a mineral acid such as hydrochloric acid.

The invention will be elucidated on the basis of the following examples, without being limited thereto.

EXAMPLE I threo-3-[-4-(methylsulphanyl)phenyl]serine amide HCL salt

By means of 570 ml of 4N caustic the pH of a solution of 221 g of glycine amide HCl salt in 1500 ml of water was brought at 12.5. At 25° C. 608 g of 4-(methyl-sulphanyl) benzaldehyde (formula 3, with n=0) in 1500 ml of methanol was added dropwise to this solution, upon which the temperature rises to 35°–40° C. 100 ml of methanol was added to the suspension. After 2–3 hours a thick suspension formed, which was stirred for 18 hours at room temperature. Subsequently, 600 ml of 4 N hydrochloric acid was added in portions to the suspension. After four hours' stirring for dissolution of all solids, extraction was effected with 2 l and 1 l of toluene, respectively. After evaporation, 400 g 4-(methylsulphanyl)benzaldehyde (66%) was recovered from the toluene extract. The water phase was evaporated to about 500 ml of thick suspension. The solids were filtered off, washed with acetone and dried. The yield was 330 g of threo-3-[4-(methylsulphanyl)-phenyl]serine amide HCl salt (63% yield=92% relative to aldehyde consumed). threo/erythro 97:3. Meltingpoint (mp) >250° C. $^1$H NMR ($D_2O$) δ 2.47 (s, 3H), 4.19 (d, 1H), 5.10 (d, 1H), 7.35 (2*d, 4H) (for erythro isomer 4.31 (d) and 5.20 (d)). In DMSO d6 the amide protons are visible at δ 7.43 and 7.96. $^{13}$C NMR (DMSO $d_6$) δ 14.54 (q), 58.20 (d), 71.10 (d), 125.41 (d), 127.36 (d), 136.56 (s), 137.51 (s), 167.83 (s). IR ($cm^{-1}$) 1699, 1486, 1039, 813, 540. Exact mass, calculated for $C_{10}H_{15}N_2O_2SCl$: 226.0776 ($M^+$, —HCl), found: 226.0780. Analysis of $C_{10}H_{15}N_2O_2SCl$: calculated C 45.71, H 5.75, N 10.66, found: C 45.4, H 5.8, N 10.6.

EXAMPLE II threo-3-[-4-(methylsulphonyl)phenyl]serine amide HCL salt

By means of 12 ml of 4N NaOH the pH of a solution of 4.4 g of glycine amide HCl salt in 5 ml of water was brought at 12.5. 15 ml of methanol was added to this solution, followed by 14.75 g of 4-(methylsulphonyl) benzaldehyde (formula 3, with n=2). To this suspension another 20 ml of methanol was added. The solution remained inhomogeneous and was stirred at room temperature for 40 hours. The thick suspension was acidified with 15 ml of 4 N hydrochloric acid. The precipitate was filtered off and resuspended in 100 ml of water. After one hour's stirring the precipitate was again filtered off. 7.5 g of impure 4-(methylsulphonyl) benzaldehyde was recovered. The collected filtrates were washed with chloroform and evaporated to a thick suspension. The solids were filtered off and washed with water and methanol and dried. Yield: 8.7 g of threo-3-[4-(methylsulphonyl)-phenyl]serine amide HCl salt (74% yield). Melting point 223°–225° C. (decomposition). $^1$H NMR ($D_2O$) 3.27 (s, 3H), 4.26 (d, 1H), 5.31 (d, 1H), 7.75 (d, 2H), 8.03 (d, 2H). (In DMSO d6 amide signals at 7.52 and 8.03. $^{13}$C NMR ($D_2O$) 43.88 (q), 59.08 (d), 71.52 (d), 128.23 (d), 128.29 (d), 139.68 (s), 145.03 (s), 169.59 (s). IR ($cm^{-1}$) 1702, 1282, 1145, 544. Exact mass (Chemical ionisation with $NH_3$), calculated for $C_{10}H_{15}N_2O_2SCl$: 241.0647 ($M^+$+ 1, —$H_2O$, —HCl), found: 241.0666. Analysis of $C_{10}H_{15}N_2O_2SCl$: calculated C 40.75, H 5.13, N 9.50, found: C 40.3, H 5.1, N 8.9.

The identical compound was prepared by oxidation of threo-3-[4-methylsulphanyl)phenyl]serine amide HCl salt: 570 mg of threo-3-[4-methylsulphanyl)phenyl]serine amide HCl salt was suspended in 10 ml of acetic acid. To this suspension, 12 ml of peracetic acid solution, this suspension, 12 ml of peracetic acid solution, prepared from 3 parts of acetic acid and 1 part of hydrogen peroxide, was added. After two hours' reacting the peroxide excess was decomposed with the aid of a Pd/C 10% catalyst. After two hours' stirring at 40° C., the Pd/C was filtered off and the solution was evaporated. The residue was washed with methanol and dried. The yield was 400 mg (62%) of a white solid that was identical to the above-mentioned compound.

EXAMPLE III
Enzymatic screening for the hydrolysis of racemic threo-3-[4-methylsulphanyl)phenyl]serine amide For screening purposes various enzyme preparations were tested (microorganisms and commercially available enzymes). The micro-organisms were partly obtained via accumulation on YCB medium with racemic threo-3-[4-methylsulphanyl)phenyl]serine amide as sole nitrogen source. Microorganisms that grew on the threo amide were isolated and, in so far as unknown, their identity was determined by means of the API test. These microorganisms were tested for stereoselectivity. To this end, 0.5 ml of a 1% solution of racemic threo amide in 50 mM of phosphate buffer (pH 6.6) was incubated for three hours at 28° C. with the 0.1 ml of cell suspension. Subsequently, the e.e. was determined of the acid that had formed and of the residual amide in the solutions (see table).

|  | e.e. (2R,3S) -amide | e.e (2S,3R) -acid |
|---|---|---|
| *Ochrobactrum anthropi* NCIB 40321 | 99% | >99% |
| Achromobacter group VD | 91% | >99% |
| *Klebsiëlla* sp. NCIB 40322 | 46% | >99% |
| *Pseudomonas carophylli* NRRL-B 11257 | 26% | >95% |
| *Klebsiëlla oxytoca* | 19% | >99% |
| *Pseudomonas putida* | 6% | 84% |

EXAMPLE IV
Enzymatic resolution of threo-3-[4-methylsulphanyl) phenyl]serine amide 7.7 g of amidase suspension from *Ochrobactrum anthropi* NCIB 40321 was added to a solution of 15.3 g of racemic threo-3-[4-methylsulphanyl)phenyl]serine amide HCl salt in 150 ml of water, brought at a pH of 5.5 with 2 ml of 4 N caustic. The solution was shaken for 18 hours at 37° C., after which the conversion according to the ammonia determination was 45–47%. The solution was acidified with 3 ml of 4 N hydrochloric acid and centrifuged at 40° C. The precipitate was stirred twice with 150 ml of water and centrifuged. The collected supernatant layers were brought at a pH of 7 and 4.6 g of 4-(methylsulphanyl)benzaldehyde was added to the solution. The solution was stirred for 15 hours at room temperature, after which the solids formed were filtered off: 8.8 g of (2R,3S)-N-[4-(methylsulphanyl) benzylidene]-3-[4-(methylsulphanyl)phenyl]serine amide (42%) with an e.e. of 94%. The filtrate was evaporated to 30 ml, following which the solids were filtered off and dried: 6.4 g of (2S,3R)-3-[4-(methylsulphanyl)-phenyl]serine (42%). E.e. >99.7%. $[\alpha]^{20}_D=-45.4°$ (c=1, 1 N HCl).

The (2R,3S) amide Schiff base (containing 5 mol % (2S,3R) acid) was converted to the (2R,3S) amide HCl salt: the Schiff base was suspended in 200 ml of chloroform/200 ml of 1N hydrochloric acid and stirred for 20 hours at room temperature. The water layer was separated and evaporated. The (2R,3S)-3-[4-methylsulphanyl)phenyl]serine amide HCl salt obtained was recrystallized from i-propanol/methanol. E.e. 99.3%. $[\alpha]^{20}_D=-9.3°$ (c=1, 1N HCl).

EXAMPLE V
Enzymatic resolution of threo-3-[4-methylsulphonyl) phenyl]serine amide at pH=6.0

3.0 g of amidase suspension from *Ochrobactrum anthropi* NCIB 40321 was added to a solution of 7.5 g of racemic threo-3-[4-methylsulphonyl)phenyl]serine amide HCl salt in 75 ml water, brought at a pH of 6.0 with 1 N caustic. The solution was shaken for 22 hours at 37° C. The pH of the solution was raised to 7 by means of 4N caustic and the solution was centrifuged at 40° C. The precipitate was stirred twice with 15 ml of water and centrifuged. 2.4 g of 4-(methylsulphonyl)benzaldehyde was added to the collected supernatant layers. The solution was stirred for 5 hours at room temperature, after which the solids formed were filtered off: 5.6 g of (2R,3S)-N-[4-(methylsulphonyl) benzylidene]-3-[4-(methylsulphonyl)phenyl]serine amide (52%). E.e. 83%. The filtrate was evaporated to 30 ml, following which the solids were filtered off: 2.3 g of (2S,3R)-3-[4-(methylsulphonyl) phenyl] serine (35%). Enantiomeric excess 99%.

EXAMPLE VI
Enzymatic resolution of threo-3-[4-(methylsulfonyl)phenyl] serine amide at pH 7.5

A solution of 2.9 gram of racemic threo-3-[4-(methylsulfonyl)phenyl]serine amide HCl-salt in 28 ml $KH_2PO_4/K_2HPO_4$ buffer (pH 7.0), was adjusted to pH 7.5 with 1 N KOH solution. To the solution was added 1.9 gram of amidase suspension (*Ochrobactrum anthropi* NCIB 40321, 10% dry weight, pH 7.0). The solution was incubated at 37° C. in a orbital shaker (170 rpm) for 71 h. During this period the pH was maintained at 7.5 by regular addition of 1 N $H_3PO_4$. After 71 h aqueous HCl (4 N) was added until the pH of the mixture was approximately 3. The enzyme was centrifuged, the palatte washed with water, and again centrifuged. The combined supernatants were adjusted to pH 7 using a 4 N NaOH solution and 0.37 gram of 4-(methylsulfonyl)benzaldehyde was added. The reaction mixture was stirred at room temperature for 2 h., then was allowed to set for 16 h. Filtration yielded 0.43 gram (10%) of crude N-[4-(methylsulfonyl)benzylidene]-3-[4-(methylsulfonyl)phenyl]serine amide. The elutant was concentrated in vacuo, the crude 3-[4-(methylsulfonyl)phenyl] serine was suspended in 5 ml of water, cooled in ice and filtered, rinsing with acetone to leave 2.07 gram (72%) 3-[4-(methylsulfonyl)phenyl]serine as a white solid. Diastereomeric ratio threo/erythro: 92:8, Enantiomeric excess threo-isomer: approx. 100% (2S,3R)-isomer.

EXAMPLE VII
Racemization of (2R,3S)-3-[4-(methylsulphanyl)-phenylserine amide 1.31 g of (2R,3S)-3-[4-(methylsulphanyl)-phenylserine amide HCl salt (e.e. 99.3%) was dissolved in 12 ml of water/methanol, 1:1. 770 mg of (methylsulphanyl) benzaldehyde was added to the solution and the pH was brought at 12.5 by means of 4N caustic. The suspension was stirred for 24 hours at 20°. Using 4N hydrochloric acid the pH of the suspension was lowered to 2, which was followed by one hour's stirring upon which the solids dissolved. The solution was washed twice with toluene. The water layer was evaporated to yield 1.15 g of cream-coloured solid. Threo/erythro ratio 97:3. E.e. 9% (2R,3S) enantiomer.

EXAMPLE VIII
Combined synthesis and racemization of threo-3-[4-methylsulphanyl) phenyl]serine amide HCl salt A suspension of 5.0 g of (2R,3S)-N-4-methyl sulphanyl) benzylidene 3-[4-methylsulphanyl)phenyl]serine amide (e.e. 94%) and 3.07 g of glycine amide. HCl in 30 ml of water was given a pH of 12.9 using 4N caustic. Then 8.1 g of 4-(methylsulphanyl)benzaldehyde in 30 ml of methanol was added. The suspension was stirred for 20 hours at 20° and processed according to the procedure given for the synthesis starting from glycine amide and 4-(methylsulphanyl)-benzaldehyde. Yield 6.85 g of threo-3-[4-(methylsulphanyl) phenyl]serine amide HCl salt (65%). E.e.<5%.

EXAMPLE IX
Synthesis of (1R,2R)-2-amino-1,3-dihydroxy-1-[4-(methylsulphanyl)phenyl]propane 2.27 g of (2S,3R)-3-[4-(methylsulphanyl) phenyl]serine was suspended in 15 ml of tetrahydrofuran (THF). After addition of 1.0 g of $NaBH_4$ the suspension was rinsed with 6 ml of THF. The thick suspension was cooled in ice and 1.23 g of $H_2SO_4$ in 3 ml of diethylether was added dropwise in 20 minutes. After 3 hours' stirring the solution was carefully acidified with 4N hydrochloric acid and washed with chloroform. The pH of the water layer was brought at 10 and 1.05 g of benzaldehyde was added. After two hours' stirring at room temperature, three extractions with chloroform were carried out. The organic layers were evaporated and heated for one hour at 80° C. with 4 N hydrochloric acid. The benzaldehyde was removed by washing twice with chloroform, following which the water layer was evaporated. 1.8 g of (1R,2R)-2-amino-1,3-dihydroxy-1-[4-(methylsulphanyl)phenyl]propane HCl salt.

What is claimed is:

1. Threo-phenylserine amide of the general formula (1),

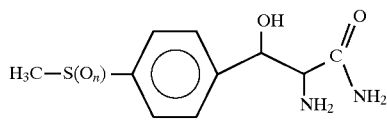

where n=0, 1 or 2 and the α-amino group is optionally protected.

2. Threo-phenylserine amide of the general formula (2),

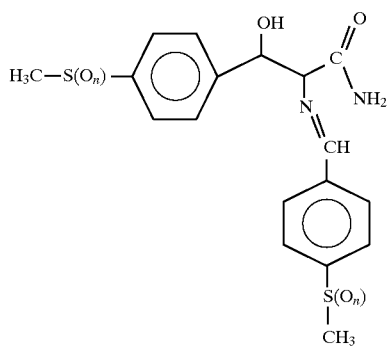

where n=0, 1 or 2.

3. A (2R, 3S)-phenylserine amide according to claim 1 or claim 2.

4. A process for the preparation of a phenylserine amide according to claim 2 in which glycine amide is contacted with the corresponding substituted benzaldehyde of formula (3)

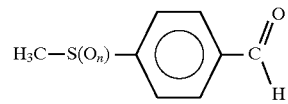

in an excess relative to the amount of glycine amide, at a pH of between 9 and 14 in the presence of a suitable solvent.

5. A process according to claim 4 in which the pH lies between 11 and 13.

6. A process according to claim 4 or 5 in which a mixture of methanol and water is used as solvent and in which the volume ratio of methanol to water lies between 1:1 and 1:2.

7. A process for the preparation of a phenylserine amide of formula 1 in which a phenylserine amide obtained by the process according to claim 4 or 5 is hydrolyzed.

8. A process for the preparation of a (2S, 3R)-phenylserine in which threo-phenylserine amide obtained by the process according to claim 7 is subjected to a stereoselective hydrolysis with the aid of an enzyme.

9. A process according to claim 8 in which the (2R, 3S)-phenylserine amide remaining after the enzymatic hydrolysis is separated and returned to the reaction mixture in which glycine amide is contacted with the substituted benzaldehyde.

10. A process according to claim 8, wherein said enzyme an amidase from *Ochrobactrum anthropi*.

11. A process according to claim 9, wherein said enzyme is an amidase from *Ochrobactrum anthropi*.

12. A process for the preparation of thiamphenicol or florfenicol comprising reducing a (2S, 3R)-3-phenylserine obtained by a process according to claim 8 to the corresponding diol in one step, said reduction being conducted in the presence of a hydride as a reducing agent; and converting the corresponding diol to thiamphenicol or florfenicol.

13. A process for the preparation of thiamphenicol or florfenicol comprising reducing a (2S, 3R)-3-phenylserine obtained by a process according to claim 9 to the corresponding diol in one step, said reduction being conducted in the presence of a hydride as a reducing agent; and converting the corresponding diol to thiamphenicol or florfenicol.

14. A process for the preparation of thiamphenicol or florfenicol comprising reducing a (2S, 3R)-3-phenylserine obtained by a process according to claim 10 to the corresponding diol in one step, said reduction being conducted in the presence of a hydride as a reducing agent; and converting the corresponding diol to thiamphenicol or florfenicol.

* * * * *

UNITED STATES PATENT AND TRADEMARK OFFICE
CERTIFICATE OF CORRECTION

PATENT NO. : 5,773,284
DATED : June 30, 1998
INVENTOR(S) : Kaptein

It is certified that error appears in the above-identified patent and that said Letters Patent is hereby corrected as shown below:

On the title page,

Please add: --[63] Continuation of PCT/NL94/00320 Dec. 16, 1994--

Signed and Sealed this

Thirteenth Day of October 1998

Attest:

BRUCE LEHMAN

Attesting Officer

Commissioner of Patents and Trademarks